US008169006B2

(12) United States Patent
Kim et al.

(10) Patent No.: US 8,169,006 B2
(45) Date of Patent: May 1, 2012

(54) BIO-SENSOR CHIP FOR DETECTING TARGET MATERIAL

(75) Inventors: Taeyoub Kim, Seoul (KR); Jong-Heon Yang, Daejeon (KR); Chang-Geun Ahn, Daejeon (KR); Chan Woo Park, Daejeon (KR); Chil Seong Ah, Daejeon (KR); Ansoon Kim, Daejeon (KR); In Bok Baek, Cheongju-si (KR); Gun Yong Sung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 307 days.

(21) Appl. No.: 12/561,032

(22) Filed: Sep. 16, 2009

(65) Prior Publication Data

US 2010/0133510 A1    Jun. 3, 2010

(30) Foreign Application Priority Data

Nov. 29, 2008    (KR) ........................ 10-2008-0120189
Dec. 22, 2008    (KR) ........................ 10-2008-0130964

(51) Int. Cl.
*G01N 27/403*    (2006.01)
(52) U.S. Cl. ........................ 257/253; 257/414; 600/579
(58) Field of Classification Search ................... 257/253
See application file for complete search history.

(56) References Cited

U.S. PATENT DOCUMENTS

| 4,064,552 | A  | * | 12/1977 | Angelucci et al. ............ 361/795 |
| 5,096,669 | A  |   | 3/1992  | Lauks et al. |
| 6,331,257 | B1 | * | 12/2001 | Loo et al. ........................ 216/13 |
| 6,709,856 | B2 |   | 3/2004  | Matsumoto et al. |
| 6,870,235 | B2 |   | 3/2005  | Abstreiter et al. |
| 7,025,774 | B2 | * | 4/2006  | Freeman et al. ............... 606/181 |
| 7,129,554 | B2 | * | 10/2006 | Lieber et al. ................... 257/414 |
| 7,177,161 | B2 | * | 2/2007  | Shima ........................... 361/816 |
| 2006/0054936 | A1 |   | 3/2006 | Lieber et al. |
| 2007/0026645 | A1 | * | 2/2007 | Lieber et al. .................. 438/478 |

FOREIGN PATENT DOCUMENTS

| JP | 3-122558    | 5/1991 |
| JP | 3-293547    | 12/1991 |
| JP | 2001-281198 | 10/2001 |
| JP | 2004-515782 | 5/2004 |

(Continued)

OTHER PUBLICATIONS

Jacobs, Ellis et al., "Analytical Evaluation of i-STAT Portable Clinical Analyzer and Use by Nonlaboratory Health-Care Professionals," *Clin. Chem.*, vol. 39(6):1069-1074 (1993).

(Continued)

*Primary Examiner* — Matthew Landau
*Assistant Examiner* — Robert Bachner
(74) *Attorney, Agent, or Firm* — Nelson Mullins Riley & Scarborough LLP; EuiHoon Lee, Esq.

(57) ABSTRACT

Provided is a bio-sensor chip. The bio-sensor chip includes a sensing part, a board circuit part, a channel part, and a cover. In the sensing part, a target material and a detection material interact with each other to detect the target material. The board circuit part is electrically connected to the sensing part. The channel part provides a solution material containing the target material into the sensing part. The cover is coupled to the board circuit part to cover the channel part and the sensing part.

20 Claims, 12 Drawing Sheets

FOREIGN PATENT DOCUMENTS

| | | |
|---|---|---|
| KR | 10-0466541 | 1/2005 |
| KR | 10-0550515 | 2/2006 |
| KR | 1020060031804 | 4/2006 |
| KR | 1020070039335 | 4/2007 |
| KR | 1020070099233 | 10/2007 |
| KR | 10-0990888 | 10/2010 |
| WO | 02/48701 A2 | 6/2002 |
| WO | 03/061569 A2 | 7/2003 |
| WO | 2005/000114 A2 | 1/2005 |
| WO | 2006/126487 A1 | 11/2006 |
| WO | 2008/087799 A1 | 7/2008 |

OTHER PUBLICATIONS

Li, Z. et al., "Sequence-Specific Label-Free DNA Sensors Based on Silicon Nanowires," *Nano Letters*, vol. 4(2):245-247 (2004).

Stern, Eric et al., "Label-free immunodetection with CMOS-compatible semiconducting nanowires," *Nature*, vol. 445:519-522 (2007).

Nair, Pradeep R. et al., "Design Considerations of Silicon Nanowire Biosensors," IEEE Transactions on Electron Devices, vol. 54(12):3400-3408 (2007).

\* cited by examiner

BIO-SENSOR CHIP FOR DETECTING TARGET MATERIAL

CROSS-REFERENCE TO RELATED APPLICATIONS

This U.S. non-provisional patent application claims priority under 35 U.S.C. §119 of Korean Patent Application No. 10-2008-0130964, filed on Dec. 22, 2008, and Korean Patent Application No. 10-2008-0120189, filed on Nov. 29, 2008, the entire contents of which are hereby incorporated by reference.

BACKGROUND

The present invention disclosed herein relates to a sensor chip, and more particularly, to a bio-sensor chip.

In general, bio-sensors are devices that measure a change by a biochemical, optical, thermal, or electrical reaction. Researches with respect to electrochemical bio-sensors are most actively conducted in recent years. The electrochemical bio-sensors may be classified into various types according to their measurement principle. One example of the various types of bio-sensors is a bio-sensor that detects biomolecules using a silicon field effect transistor (FET) principle.

The bio-sensor using the FET principle senses a change of conductivity generated during an interaction between a target molecule and a sensing molecule in a silicon nano-wire to detect a specific bio-material. Since the bio-sensor has high sensitivity, more research is being done.

It may be expected to apply the bio-sensor to overall industry including the medical world as well as a home. Thus, manufacturing costs should be lowered, and a manufacturing process should be simplified to provide a bio-sensor at a relatively low price. Also, a target material should be efficiently transferred to the sensor to stably read an electrical signal.

The bio-sensor needs to use a device such as a centrifugal separator in order to separate the target material. Moreover, the bio-sensor uses a syringe pump to move a material containing the target material from the outside into the inside of the sensor. Thus, there are limitations that the bio-sensor is not easy to carry around. Particularly, when the sensing material is measured, the expensive and bulky syringe pump may become a big drag on commercialization of the bio-sensor.

SUMMARY

An embodiment of the present invention provides a bio-sensor chip that is easy to carry around.

An embodiment of the present invention also provides a bio-sensor chip that has low manufacturing costs and is easy to use.

Embodiments of the present invention provide bio-sensor chips including a field effect transistor (FET) sensing part in which a silicon nano-wire is disposed, a transparent channel part including a fluid channel, a printed circuit board, and a transparent cover.

In other embodiments of the present invention, bio-sensor chips include: a sensing part in which a target material and a detection material interact with each other to detect the target material; a board circuit part electrically connected to the sensing part; a channel part providing a solution material containing the target material into the sensing part; and a cover coupled to the board circuit part to cover the channel part and the sensing part.

In some embodiments, the cover may include a solution inlet and a solution outlet, which provide input/output paths through which the solution material flows into/from the channel part.

In other embodiments, the cover may be formed of one of polymethylmethacrylate, polycarbonate, cyclic olefine copolymer, polyethylene sulfone, polystyrene, and combinations thereof.

In still other embodiments, the channel part may include: a channel inlet vertically aligned with the solution inlet to provide a flow path of the solution material from the solution inlet toward the sensing part; a channel outlet vertically aligned with the solution outlet to provide a flow path of the solution material from the sensing part toward the solution outlet; and a fluid channel extending from the channel inlet up to the channel outlet to restrict the flow path of the solution material to the sensing part.

In even other embodiments, the channel part may include a transparent body formed of polydimethylsiloxane.

In yet other embodiments, the sensing part may include: a semiconductor substrate; and a sensor having a detection material disposed on the semiconductor substrate, wherein the sensor contacts the solution material provided through the channel inlet such that the detection material interacts with the target material within the solution material.

In further embodiments, the board circuit part may include: an upper chip guide including a guide groove for guiding a position of the sensing part; and a lower circuit board electrically connected to the sensing part to input/output an electrical signal of the sensing part.

In still further embodiments, the board circuit part may include a coupling groove for coupling the cover thereto, and the cover may include a coupling protrusion inserted into the coupling groove.

In other embodiments of the present invention, bio-sensor chips include: a sensing part including a sensor in which a detection material is fixed and a semiconductor substrate on which the sensor is disposed; a channel part providing a solution material containing a target material interacting with the detection material into the sensing part to contact the solution material with the sensor; a board circuit part electrically connected to the sensing part to input/output an electrical signal between an external device and the sensing part; and a cover covering the board circuit part to provide a space in which the sensing part and the channel part are disposed, the cover providing input/output paths of the solution material.

In some embodiments, the cover may include a first transparent cover having a first inlet and a first outlet providing input/output paths through which the solution material flows into/from the channel part.

In other embodiments, the cover may further include a second transparent cover covering the first transparent cover. The second transparent cover may include: a flow channel providing a flow path of the solution material; a filter filtering the solution material; a second inlet and a second outlet, which provide input/output paths through which the filtered solution material flows into/from the first transparent cover; and a storage container storing the solution material discharged through the second outlet.

In still other embodiments, the sensor may include: a plurality of sensor groups independently detecting protein makers different from each other; and at least one sensor group obtaining a reference signal of an electrical signal change of the sensing part.

In even other embodiments, the board circuit part may include: a chip guide including a guide groove for guiding a position of the sensing part; an upper circuit board including a substrate bias pad connected to the semiconductor substrate of the sensing part using a conductive double-sided adhesive tape and a bonding pad connected to the sensing part using a bonding wire; and a lower circuit board including a first layer including a plurality of electrical interconnections connected to the substrate bias pad and the bonding pad and a second layer including a plurality of connection pads connected to the plurality of electrical interconnections.

In still other embodiments of the present invention, bio-sensor chips include: a sensing part including a plurality of nano-wire sensors in which a detection material is fixed and a semiconductor substrate on which the plurality of nano-wire sensors are disposed; a transparent channel part guiding a solution material containing a target material interacting with the detection material such that the solution material crossly flows through the plurality of nano-wire sensors; a board circuit part electrically connected to the sensing part to input/output an electrical signal between an external device and the sensing part; a lower transparent cover covering the board circuit part to provide a space in which the sensing part and the channel part are disposed; and an upper transparent cover covering the lower transparent cover.

In some embodiments, the lower transparent cover may include a lower solution inlet and a lower solution outlet, which provide input/output paths through which the solution material flows into/from the transparent channel part.

In other embodiments, the upper transparent cover may include: an upper solution inlet and an upper solution outlet, which are vertically aligned with the lower solution inlet and the lower solution outlet, respectively; a filter filtering the solution material provided into the upper solution inlet; a storage container storing the solution material discharged from the upper solution outlet; a first solution flow channel providing a flow path of the solution material from the filter toward the upper solution inlet; and a second solution flow channel providing a flow path of the solution material from the upper solution outlet toward the storage container.

In still other embodiments, the transparent channel part may include: a channel solution inlet and a channel solution outlet, which are vertically aligned with the lower solution inlet and the lower solution outlet, respectively; and a fluid channel extending from the channel solution inlet up to the channel solution outlet to allow the solution material to flow on the plurality of nano-wire sensors.

In even other embodiments, the nano-wire sensor may include: a silicon nano-channel doped with impurities contacting with the solution material; and a source/drain disposed at both sides of the silicon nano-channel.

In yet other embodiments, the board circuit part may include: an upper chip guide comprising a guide groove for guiding a position of the sensing part and a coupling groove for coupling the lower transparent cover thereto; and a lower printed circuit board comprising an internal connection pad connected to the sensing part, an electrical interconnection electrically connected to the internal connection pad, and an external connection pad connected to the electrical interconnection and an external device.

In further embodiments, the lower transparent cover may include a coupling protrusion inserted into the coupling groove.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF EMBODIMENTS

Figure 1:
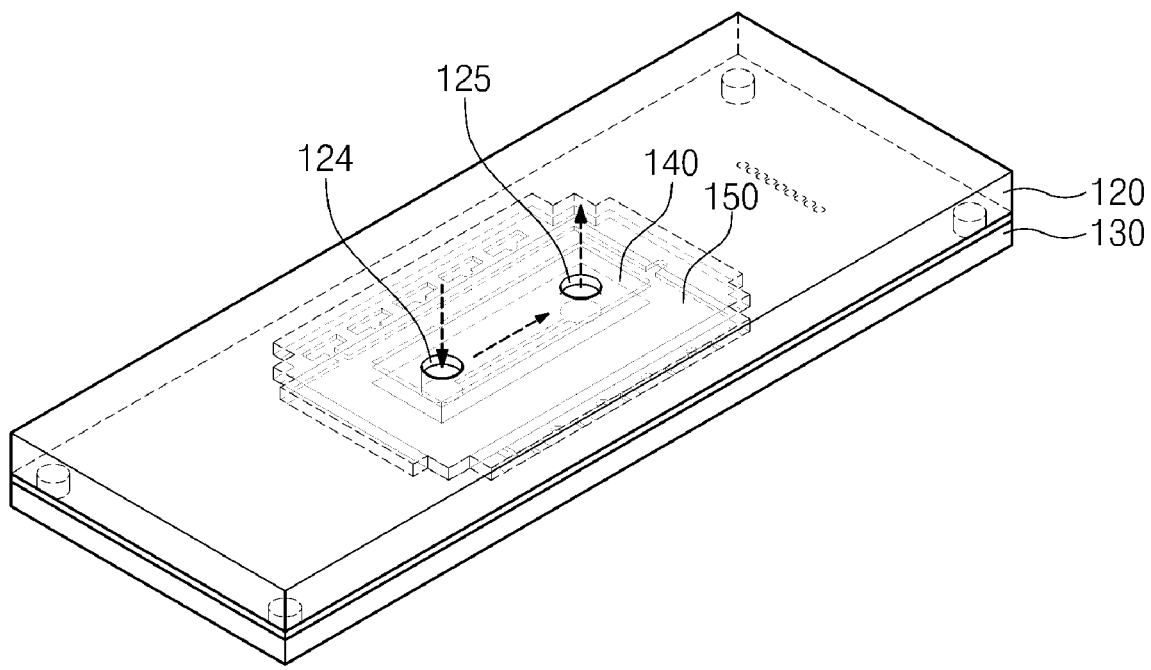
FIG. 1 is a perspective view of a bio-sensor chip according to an embodiment of the present invention.

Hereinafter, a bio-sensor chip according to an embodiment of the present invention will be described in detail with reference to the accompanying drawings.

Advantages of the present invention in comparison with the related art will be clarified through the Detailed Description of Preferred Embodiments and the Claims with reference to the accompanying drawings. In particular, the present invention is well pointed out and clearly claimed in the Claims. The present invention, however, may be best appreciated by referring to the following Detailed Description of Preferred Embodiments with reference to the accompanying drawings. In the drawings, like reference numerals refer to like elements throughout.

Embodiment

FIG. 1 is a perspective view of a bio-sensor chip according to an embodiment of the present invention.

Referring to FIG. 1, a bio-sensor chip 100 according to an embodiment of the present invention includes a sensing part 150, a channel part 140, a cover 120, and a board circuit part 130. The sensing part 150 senses a target material contained in a solution material introduced from the outside. The channel part 140 moves the solution material containing the target material into the sensing part 150. The cover 120 covers the sensing part 150 and the channel part 140. The board circuit part 130 is electrically connected to the sensing part 150 to transmit electrical input/output signals between the sensing part 150 and an external device (e.g., reader).

The solution material containing the target material is provided from the outside into the bio-sensor chip 100 through a solution inlet 124 and discharged from the inside of the bio-sensor chip 100 into the outside through a solution outlet 125. The solution material provided inside the bio-sensor chip 100 may be provided into the sensing part 150 by the channel part 140 to sense a specific component. Dot-dash arrows of FIG. 1 denote a moving path of the solution material. According to an embodiment of the present invention, the solution material may include a solution diluted with blood, blood serum, or blood plasma.

Figure 2:
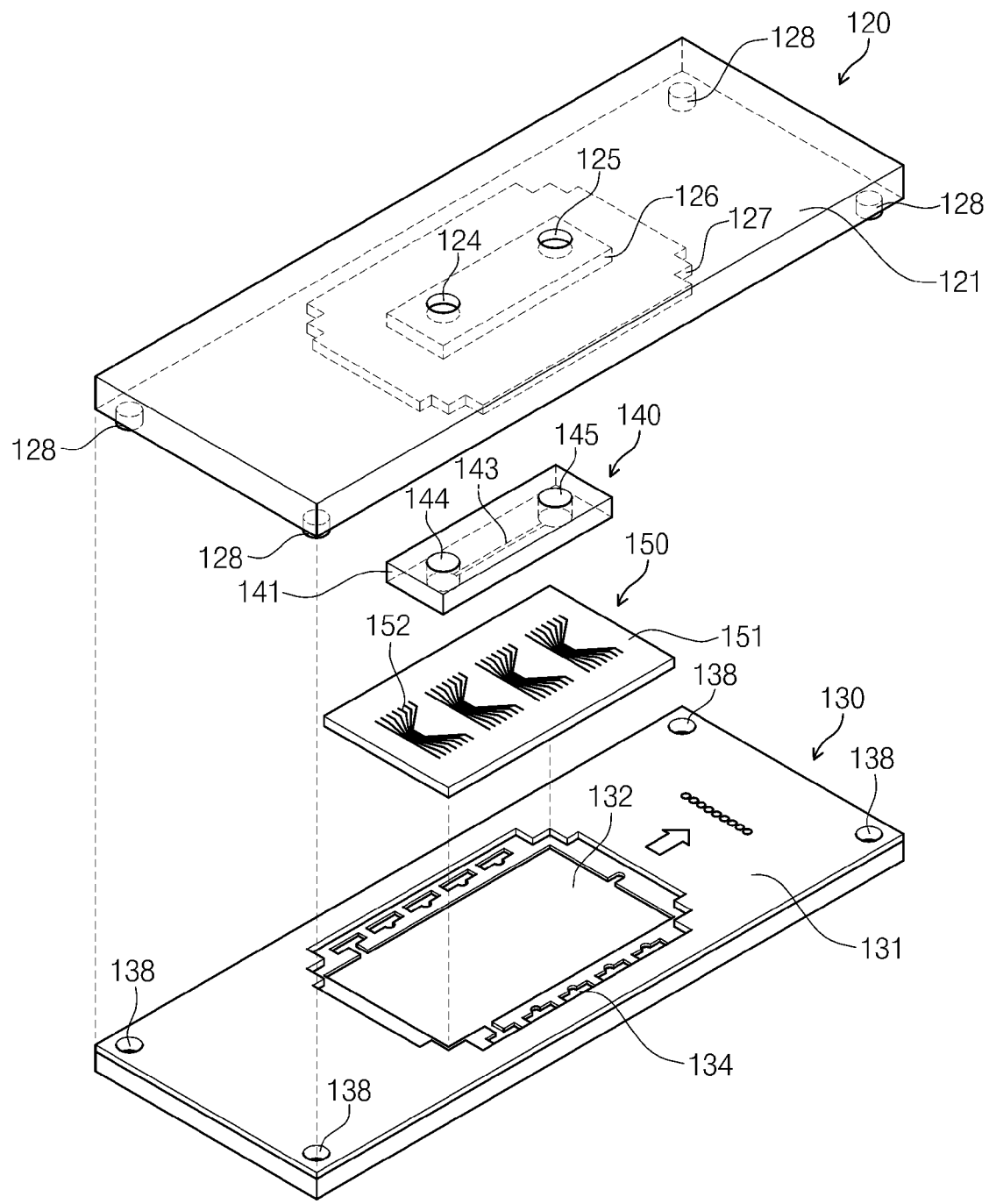
FIG. 2 is an exploded perspective view of a bio-sensor chip according to an embodiment the present invention.

FIG. 2 is an exploded perspective view of a bio-sensor chip according to an embodiment the present invention.

Referring to FIG. 2, the cover 120 may be coupled to the board circuit part 130. For this, the cover 120 may include coupling protrusions 128, and coupling grooves 138 into which the coupling protrusions 128 are inserted. For example, the cover 120 may have a rectangular shape, and the coupling protrusions 128 may be disposed on four edges of the rectangular shape, respectively. Similarly, the board circuit part 130 may have a rectangular shape, and the coupling grooves 138 may be defined in four edges of the board circuit part 130, respectively, so that the coupling grooves 138 are vertically aligned with the coupling protrusions 128. Since the coupling protrusions 128 are inserted into the coupling grooves 138, the cover 120 is coupled to the board circuit part 130. Hence, the sensing part 150 and the channel part 140 may be smoothly aligned and disposed between the cover 120 and the board circuit part 130.

The sensing part 150 and the sensing part 150 may be provided between the cover 120 and the board circuit part 130. The sensing part 150 may sense a detection material (target material) of the solution material provided from the outside. The channel part 140 may provide the solution material containing the target material provided through the solution inlet 124 to the sensing part 150. The sensing part 150 may be electrically connected to the board circuit part 130, and the channel part 140 may be placed on the sensing part 150.

When the solution material, e.g., the blood may be provided into the channel part 140 through the solution inlet 124, the blood may be provided into the sensing part 150 by the channel part 140 to react to the sensing material contained in the sensing part 150. The blood is discharged through the solution outlet 125 after the blood reacts to the sensing material.

Figure 3:
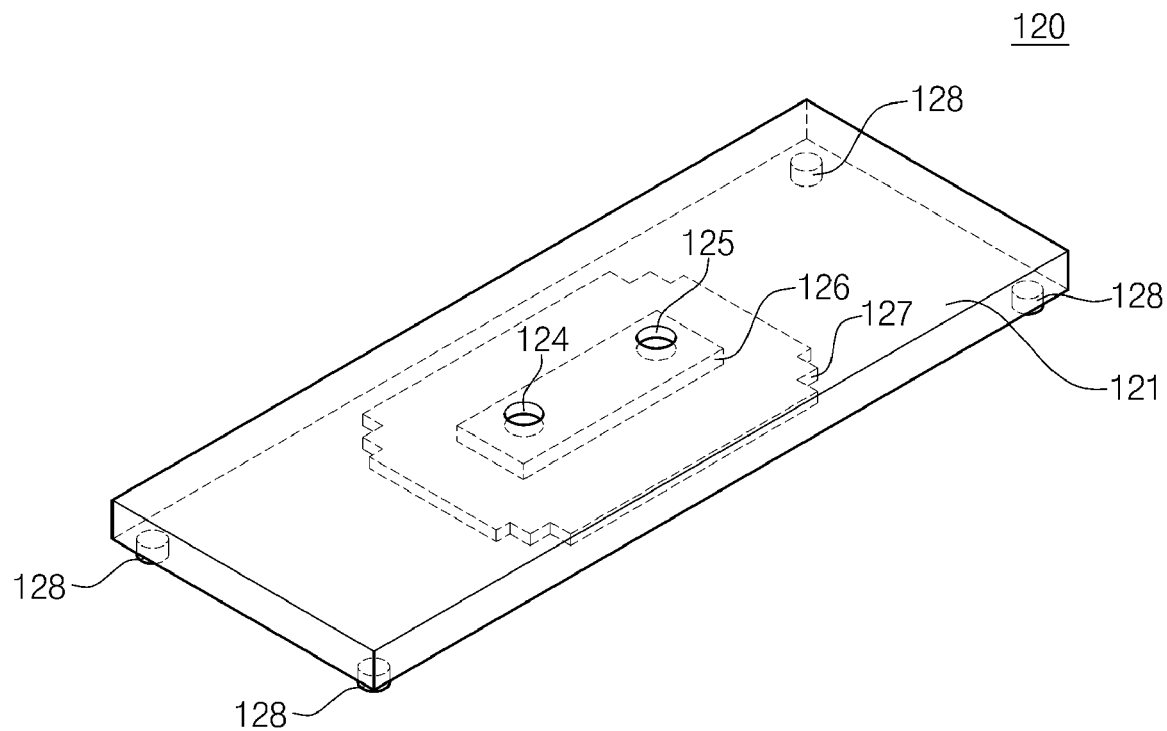
FIG. 3 is a perspective view illustrating a cover of a bio-sensor chip according to an embodiment the present invention.

FIG. 3 is a perspective view illustrating a cover of a bio-sensor chip according to an embodiment the present invention.

Referring to FIGS. 2 and 3, the cover 120 may cover the channel part 140 and the sensing part 150 such that the cover 120 may protect the channel part 140 and the sensing part 150 against the outside. Also, the cover 120 may press the channel part 140 at a predetermined pressure to realize a strong coupling between the channel part 140 and the sensing part 150. Thus, it may prevent the solution material flowing along the channel part 140 from leaking. Accordingly, the cover 120 may have a structure designed to fix positions of the channel part 140 and the sensing part 150. For example, the cover 120 may have a structure that may provide a space 126 into which the whole channel part 140 or an upper portion of the channel part 140 may be inserted and a space 127 into which the sensing part 150 may be inserted. The space 127 may further include a space for protecting a wire bonding for electrically connecting the sensing part 150 to the board circuit part 130. These spaces 126 and 127 may be defined by an engraved pattern.

A body 121 of the cover 120 may be formed of a transparent material to easily observe a flow state or leak state of the solution material, an alignment state between the sensing part 150 and the channel part 140, an electrical connection state between the sensing part 150 and the board circuit part 130, etc. For example, the transparent material constituting the body 121 of the cover 120 may include a transparent plastic such as polymethylmethacrylate (hereinafter, referred to as a "PMMA").

The PMMA is a kind of thermoplastic acryl resins and is widely used as a substitute of glass. The PMMA is generally easy to handle and inexpensive. In addition, since the PMMA is a thermoplastic material, it may be easily manufactured to a desired shape. That is, when a pressure is applied to the heated PMMA disposed on a metal mold, a plastic pattern having a shape opposite to that of the mold may be formed. The transparent material constituting the body 121 of the cover 120 may include one of polycarbonate, cyclic olefine copolymer, polyethylene sulfone, polystyrene, and combinations thereof.

The solution inlet 124 and the solution outlet 125 may be provided in the cover 120. For example, the solution inlet 124 and the solution outlet 125 may pass through the body 121 of the cover 120 and have vertically opened shapes, respectively.

Figure 4A:
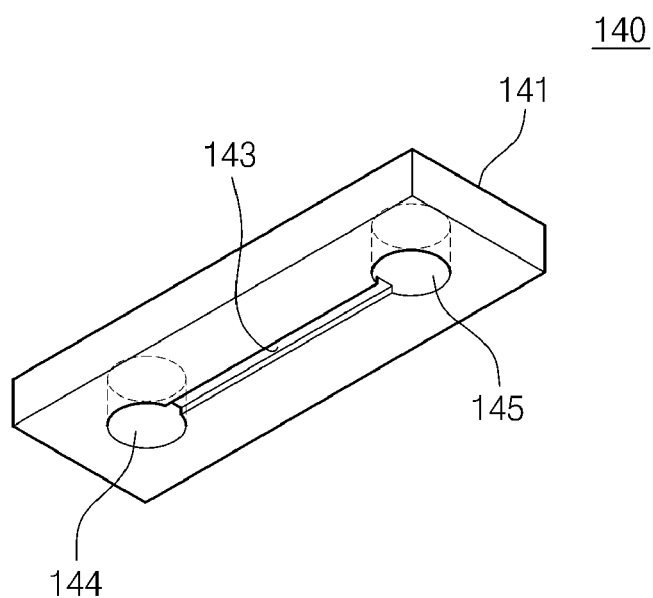
FIG. 4A is a perspective view illustrating a channel part of a bio-sensor chip according to an embodiment of the present invention.
Figure 4B:
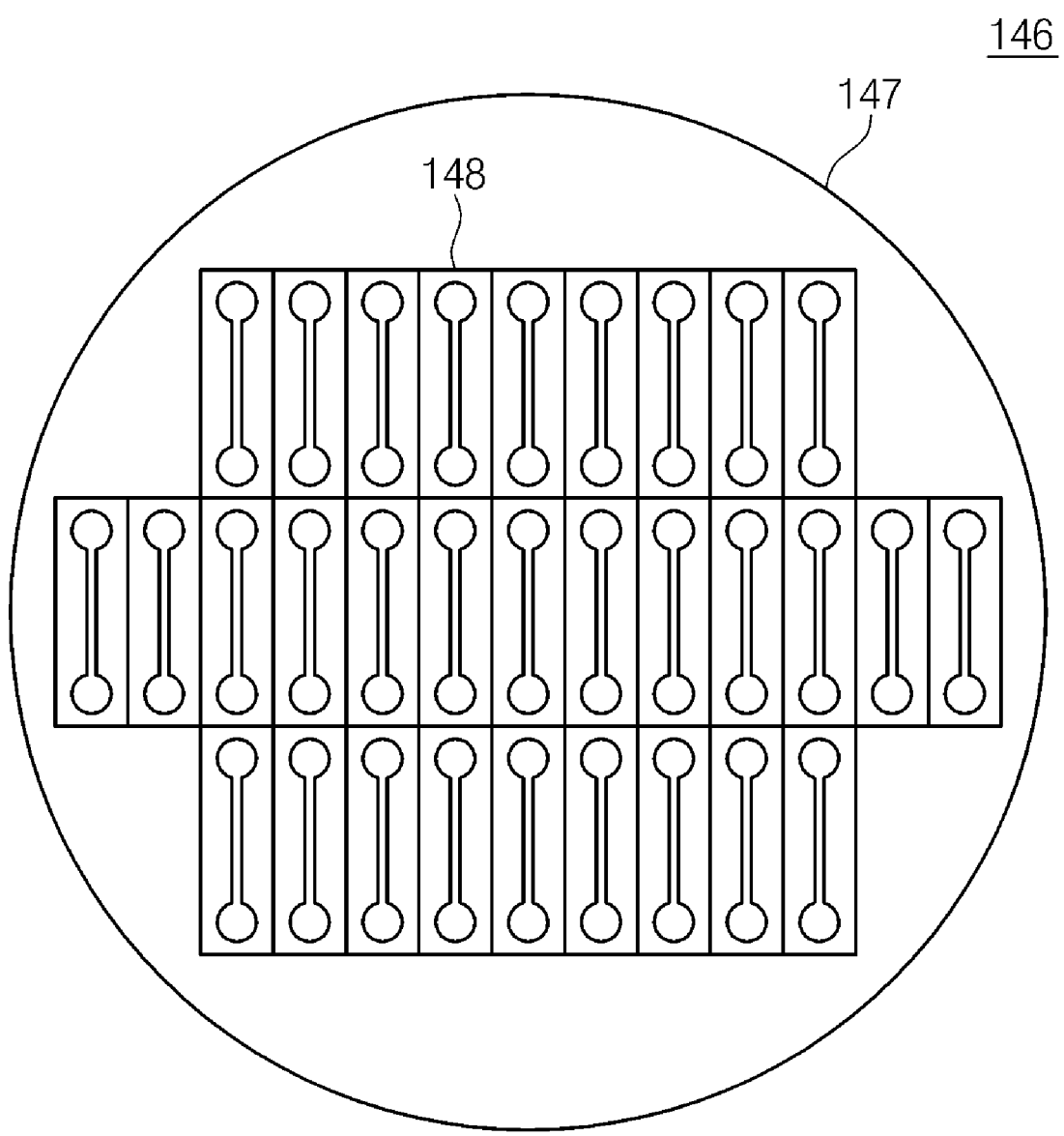
FIG. 4B is a plan view of a mold for manufacturing a channel part of a bio-sensor chip according to an embodiment of the present invention.

FIG. 4A is a perspective view illustrating a channel part of a bio-sensor chip according to an embodiment of the present invention, and FIG. 4B is a plan view of a mold for manufacturing a channel part of a bio-sensor chip according to an embodiment of the present invention;

Referring to FIGS. 2 and 4A, the channel part 140 may guide the solution material such that the solution material flows through a desired path. The channel part 140 includes a fluid channel 143, a channel solution inlet 144, and a channel solution outlet 145. The fluid channel 143 provides a path through which the solution material flows. The channel solution inlet 144 is provided at one end of the fluid channel 143 to provide a path through which the solution material provided into the fluid channel 143 is introduced. The channel solution outlet 145 provides a path through which the solution material passing through the fluid channel 143 is discharged. The fluid channel 143, the channel solution inlet 144, and the channel solution outlet 145 are formed in the body 141 to define the channel part 140. The channel solution inlet 144 and the channel solution outlet 145 may pass through the body 141 and have vertically opened shapes, respectively. The channel solution inlet 144 and the channel solution outlet 145 may be vertically aligned with the solution inlet 124 and the solution outlet 125, respectively. In addition, the channel solution inlet 144 and the channel solution outlet 145 may have the same size as the solution inlet 124 and the solution outlet 125, respectively. As a result, the solution material may smoothly flow between the cover 120 and the channel part 140.

The channel part 140 is in contact with the sensing part 150 disposed below thereof and may be pressed at a predetermined force by the cover 120 disposed over thereof to prevent the solution material flowing into the fluid channel 143 from leaking. Thus, the body 141 of the channel part 140 may have elasticity and be formed of a transparent material, e.g., polydimethylsiloxane (hereinafter, referred to as a "PDMS") to easily observe a flow state or leak state of the solution material and an alignment state between the sensing part 150 and the channel part 140. The PDMS may be a silicon-based organic polymer widely used as a medical appliance such as a contact lens and include a bio-compatible material.

Referring to FIG. 4B, since the bio-compatible material is filled into the mold and then is hardened to manufacture the PDMS, a mold 146 having a shape opposite to a desired shape may be firstly manufactured to form the channel part 140. For example, a pattern 148, e.g., an Su-8 pattern (a pattern by using Su-8 photoresist commercially available from Microchem Company which is applied as a negative-type photoresist in order to form a microstructure) may be formed on a 4-inch silicon wafer 147 using a MEMS process to manufacture the PDMS mold 146. Thus, the channel part 140 may be mass producible.

Again referring to FIG. 4A, a cross-section of the fluid channel 143 may affect a flow speed of the solution material and also affect a volume interacting with the sensing part 150 per unit volume in the total flow amount of the solution material. Thus, considering these facts, the cross-section of the fluid channel 143 may be designed in a suitable size in which a target molecule (the target material) may interact with a probe molecule (the sensing material). For example, the fluid channel 143 may have a tetragonal shape (e.g., a rectangular shape) in section and may be restrictively disposed on a lower portion of the body 141 that is in contact with the sensing part 150.

Figure 5A:
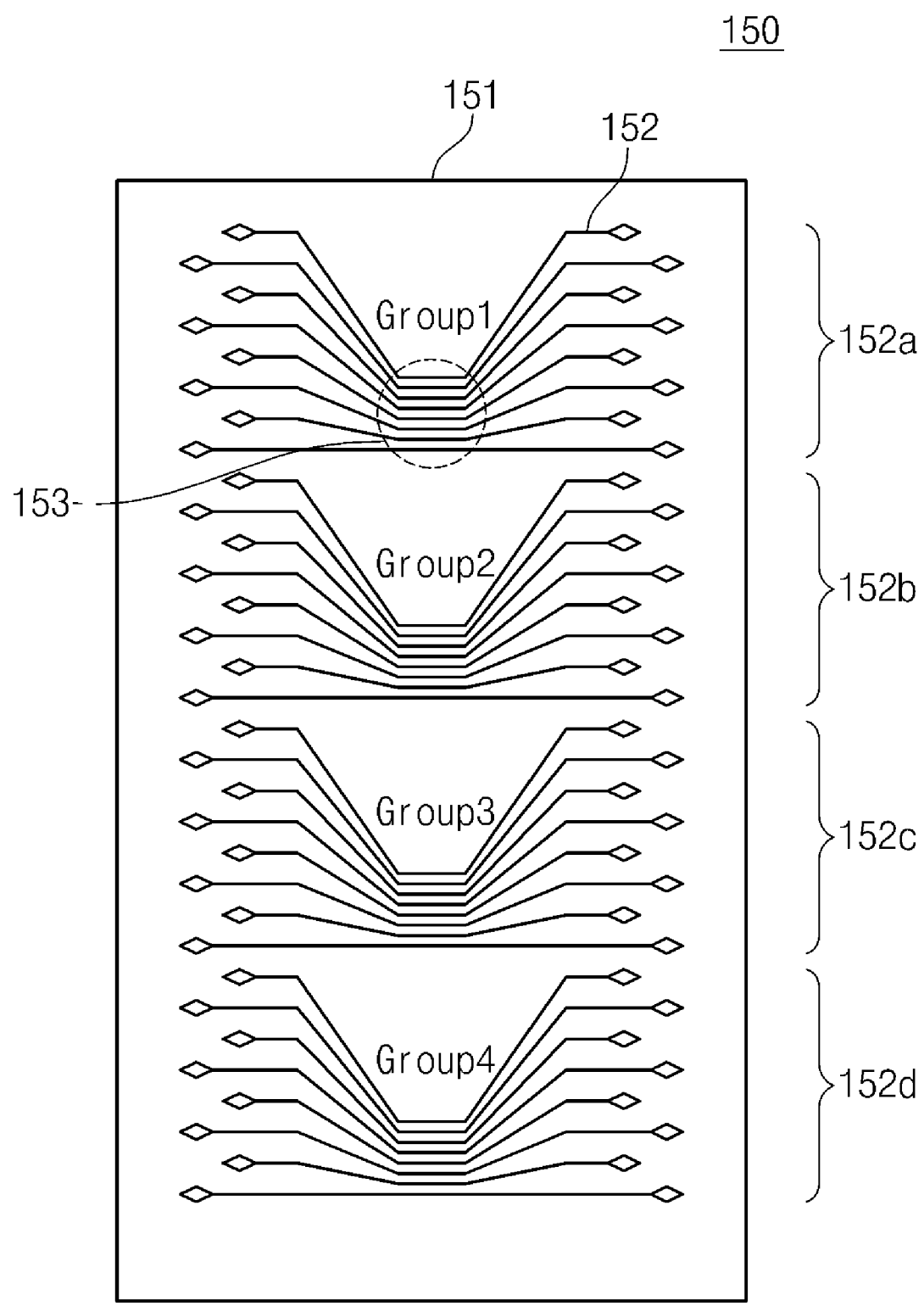
FIG. 5A is a plan view illustrating a sensing part of a bio-sensor chip according to an embodiment of the present invention.
Figure 5B:
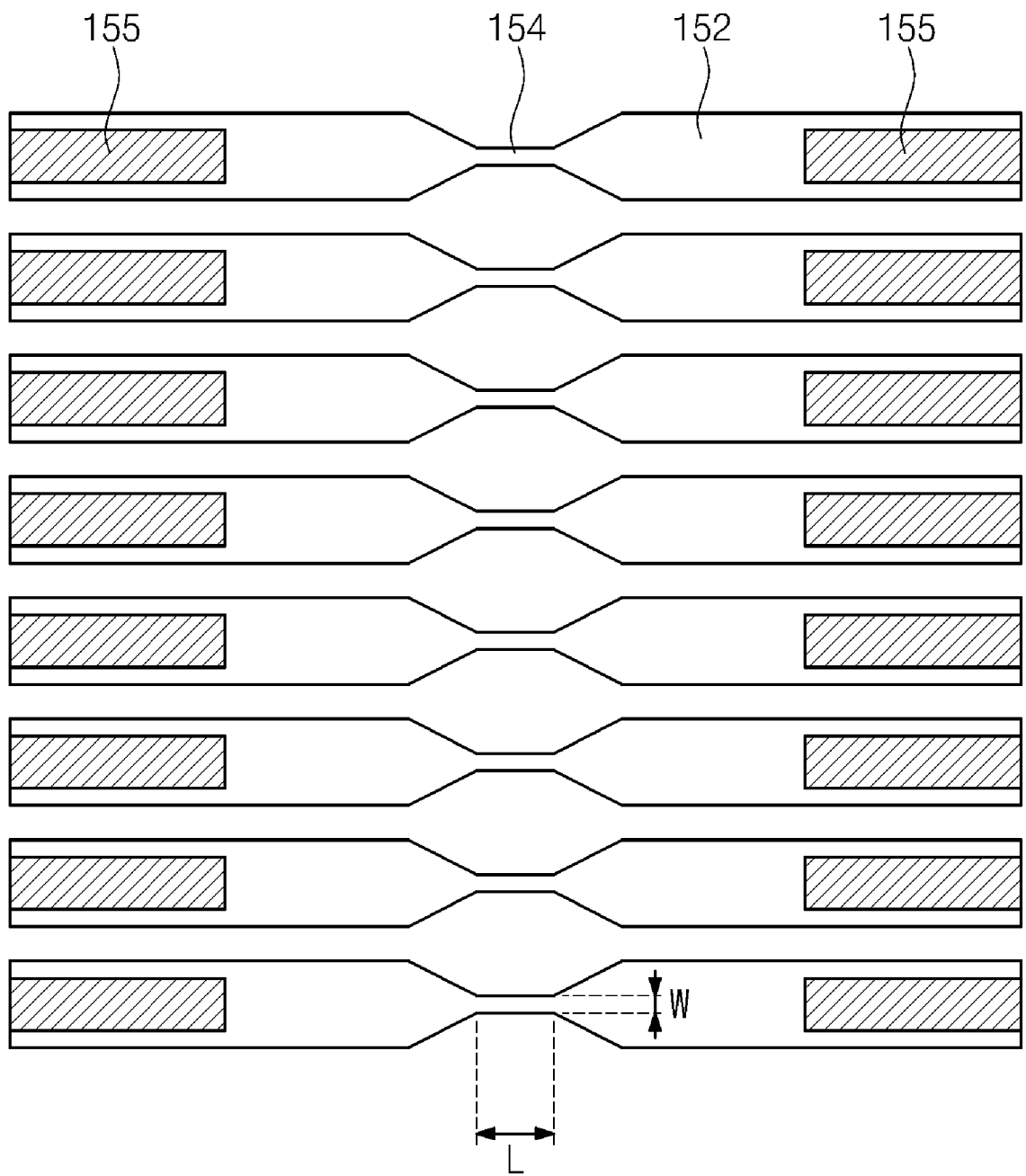
FIG. 5B is an enlarged plan view illustrating sensors of a bio-sensor chip according to an embodiment of the present invention.

FIG. 5A is a plan view illustrating a sensing part of a bio-sensor chip according to an embodiment of the present invention, and FIG. 5B is an enlarged plan view illustrating sensors of a bio-sensor chip according to an embodiment of the present invention.

Referring to FIGS. 2 and 5A, the sensing part 150 may include a plurality of sensors 152 on a semiconductor substrate 151. The sensing part 150 may have a size of approximately 15 mm×25 mm. The solution material provided through the channel solution inlet 144 of the channel part 140 is guided by the fluid channel 143 to pass through the sensors 152. At this time, the sensors 152 may detect the target material in the flowing solution material.

The semiconductor substrate 151 may include a silicon-on-insulator (SOI) substrate. The sensors 152 may be designed to detect target materials different from each other. For example, the sensors 152 may be divided into a plurality of groups, e.g., a first group 152a, a second group 152b, and a third group 152c, and a fourth group 152d. The first to third groups 152a to 152c may independently detect three different types of protein markers, and the fourth group 152d may obtain a reference signal of an electrical signal change of the sensing part 150. Each of the four groups 152a to 152d may include, e.g., eight sensors 152. FIG. 5B is a view of a portion 153 of the sensors 152.

Referring to FIG. 5B, each of the sensors 152 may include a silicon nano-wire. For example, each of the sensors 152 may include a nano-channel 154 and a source/drain 155 disposed at both sides of the nano-channel 154. The nano-channel 154 may have a height within the range of several ten nm (a thickness of the semiconductor substrate 151). The nano-channel 154 may be formed of silicon doped with a P-type or an N-type dopant. An antibody (sensing material) specifically coupled to the marker (detection material) to be detected may be fixed to a surface of the nano-channel 154 through a bio-surface reaction. The sensors 152 of the respective groups 152a to 152d may have the same channel width W and length L as each other. For example, the nano-channel 154 may have the width W within the range of several ten nm to several hundred nm and the length L within the range of about 2 to about 20 nm. The source/drain 155 may be formed of a metal electrode such as Au, Au/Cr, Au/Ti, and Au/Cr/Al. An external voltage may be applied to the nano-channel 154 through the source/drain 155. Alternatively, the sensors 150 may be configured as disclosed in U.S. Pat. No. 6,870,235, or U.S. Published Patent Application No. 2006/0054936, the entire contents of which are hereby incorporated by reference.

Figure 6A:
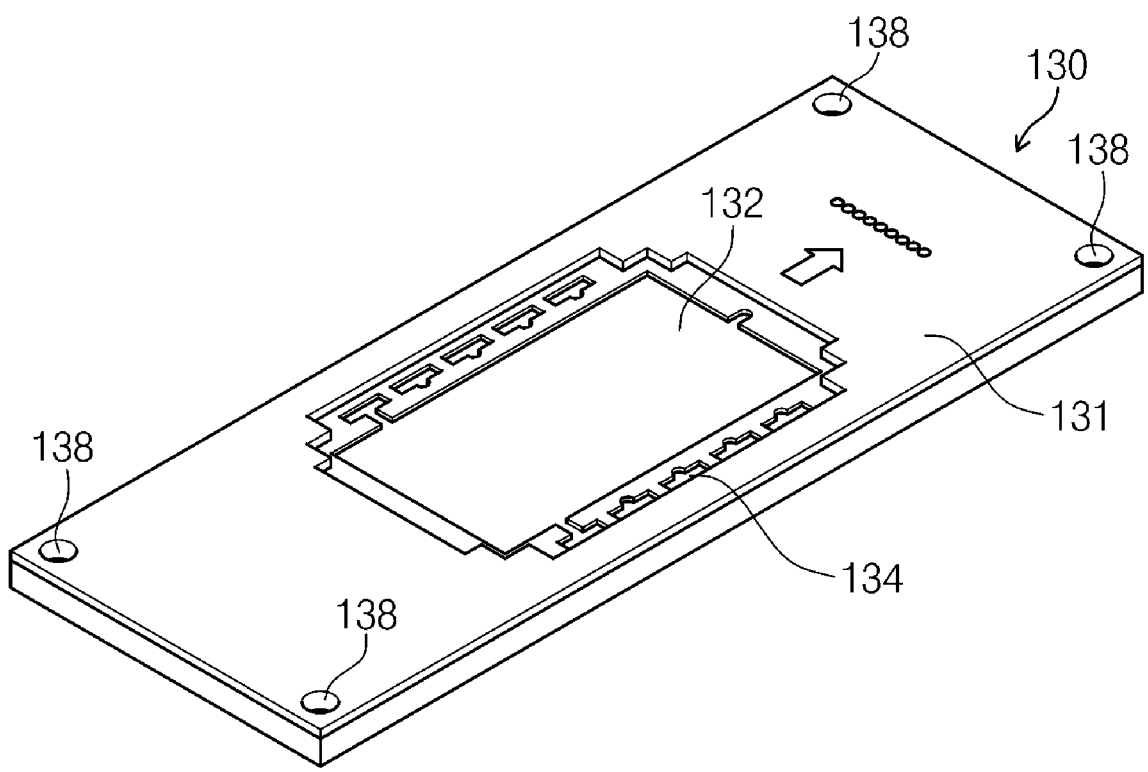
FIG. 6A is a perspective view illustrating a board circuit part of a bio-sensor chip according to an embodiment of the present invention.
Figure 6B:
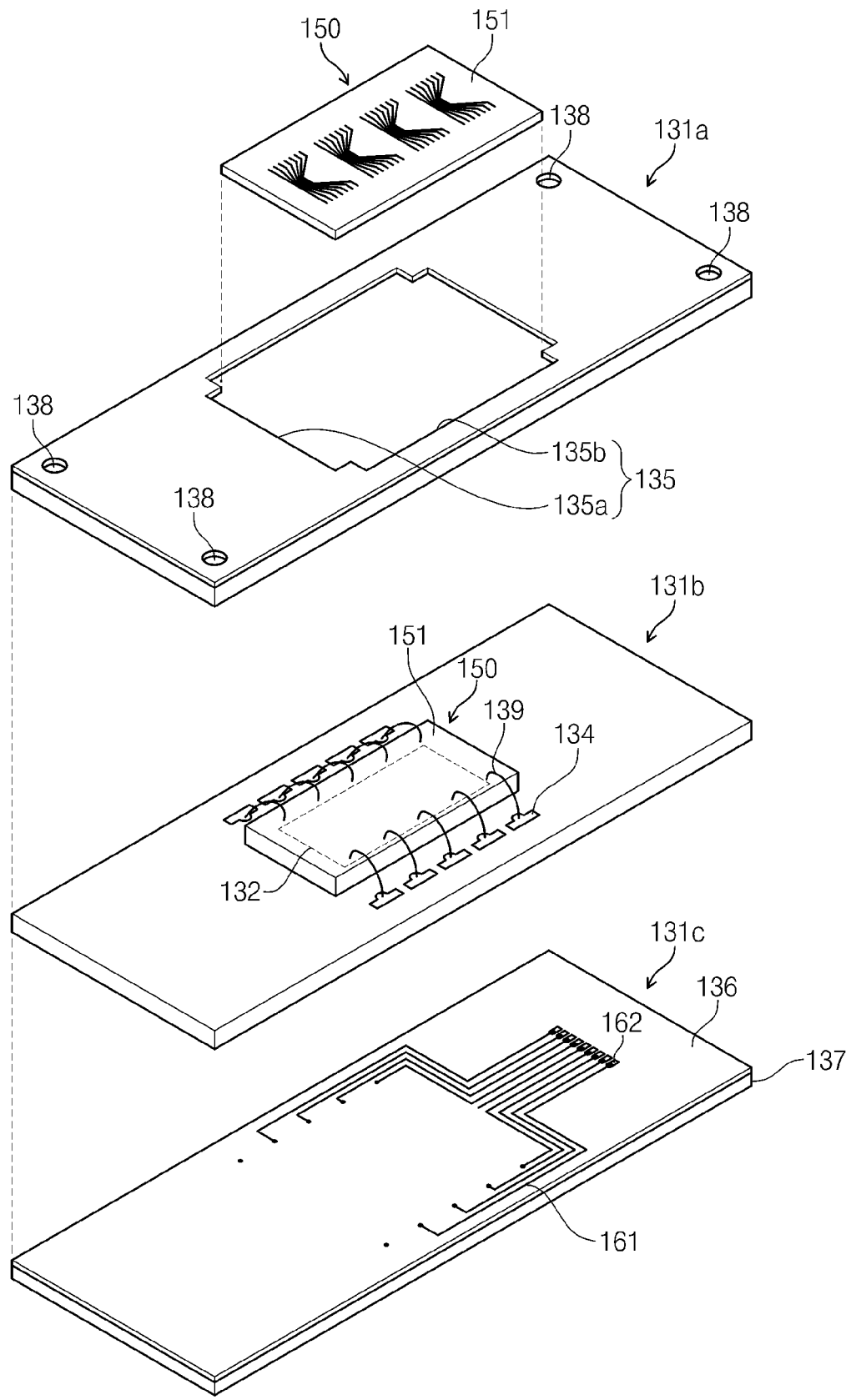
FIG. 6B is an exploded perspective view illustrating a board circuit part of a bio-sensor chip according to an embodiment of the present invention.

FIG. 6A is a perspective view illustrating a board circuit part of a bio-sensor chip according to an embodiment of the present invention, and FIG. 6B is an exploded perspective view illustrating a board circuit part of a bio-sensor chip according to an embodiment of the present invention.

Referring to FIGS. 2 and 6A, the board circuit part 130 may provide a place in which the sensing part 150 is packaged. The board circuit part 130 may input/output the electrical signal generated in the sensing part 150. The board circuit part 130 may be configured to be compatible with an external device such as the reader. For example, the board circuit part 130 may include a printed circuit board 131 having a substantially rectangular shape with a size of a slide glass, i.e., a size of about 76 mm×25 mm. For example, a glass fiber including an epoxy resin may be folded over and over again to manufacture the printed circuit board 131. The printed circuit board 131 may have elasticity and a characteristic having a certain degree of flexibility such that a compressive force is not concentrated at the sensing part 150 but dispersed when the printed circuit board 131 is coupled to the cover 120 for packaging. As describe above, the coupling grooves 138 into which the coupling protrusions 128 are inserted may be defined in four edges of the printed circuit board 131, respectively.

The printed circuit board 131 may include internal connection pads 132 and 134 electrically connected to the sensing part 150, and a guide groove 135 exposing the internal connection pads 132 and 134 and guiding an alignment position of the sensing part 150. The printed circuit board 131 may have a single layer structure using one layer or a multilayer structure in which several layers are folded over and over again. According to the embodiment of the present invention, the printed circuit board 131 may have the multilayer structure as described later with reference to FIGS. 6C to 6F.

Referring to FIG. 6B, for example, the printed circuit board 131 may have the multilayer structure including an upper chip guide 131a guiding the sensing part 150 in position, and circuit boards 131b and 131c on which electrical circuits are disposed. The circuit boards 131b and 131c may include an upper circuit board 131b electrically connected to the sensing part 150 and a lower circuit board 131c electrically connected to the external device, e.g., the reader.

Figure 6C:
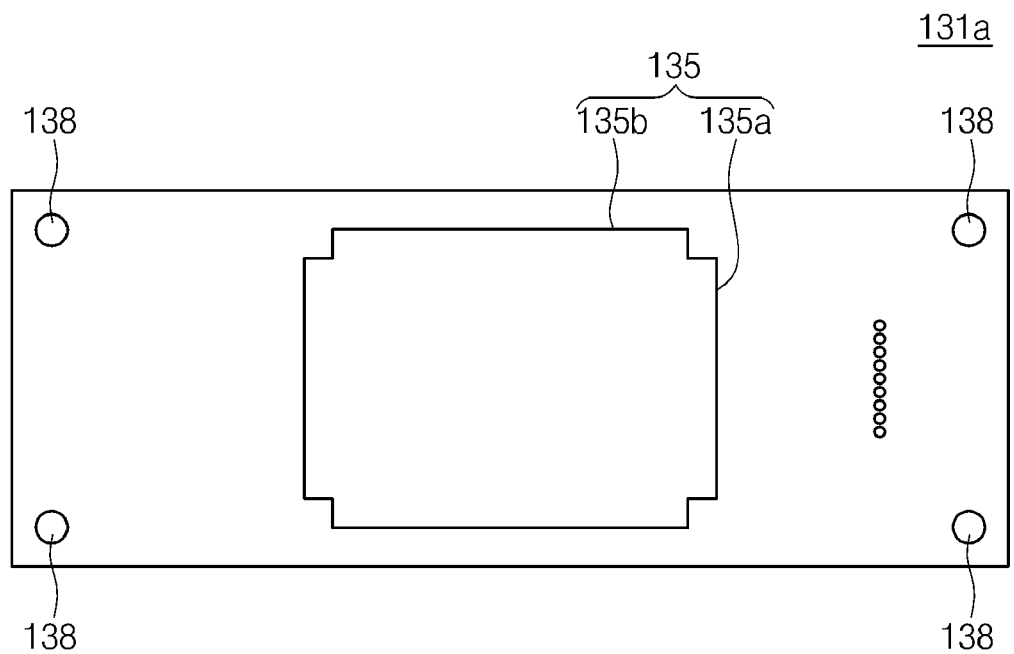
FIG. 6C is a plan view illustrating an upper chip guide of a board circuit part in a bio-sensor chip according to an embodiment of the present invention.
Figure 6D:
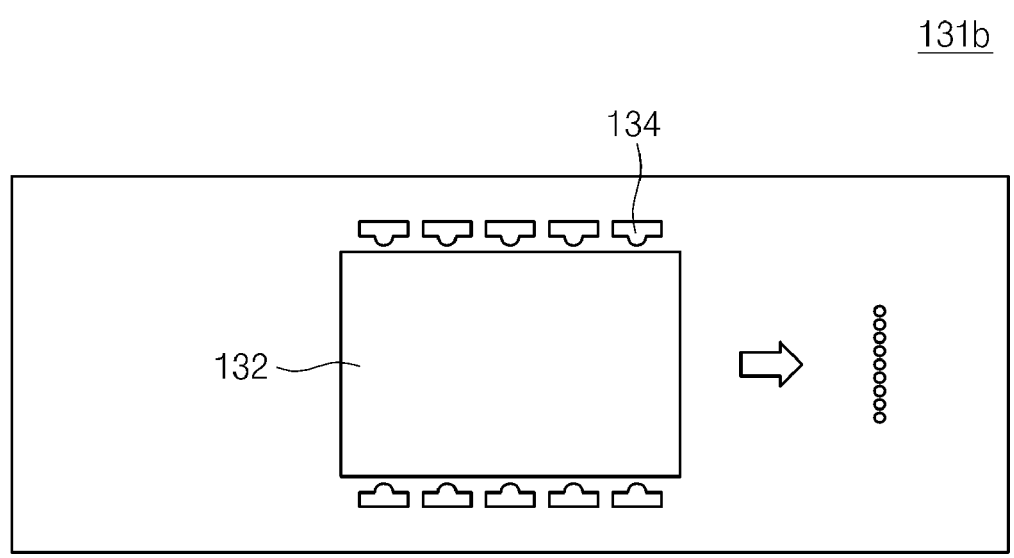
FIG. 6D is a plan view illustrating an upper circuit board of a board circuit part in a bio-sensor chip according to an embodiment of the present invention.
Figure 6E:
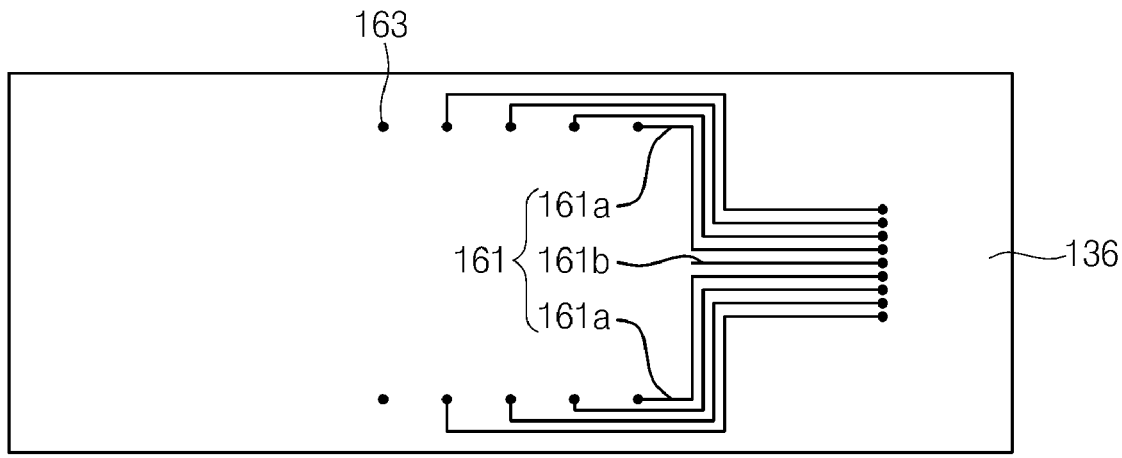
FIGS. 6E and 6F are plan views illustrating a lower circuit board of a board circuit part in a bio-sensor chip according to an embodiment of the present invention.
Figure 6F:
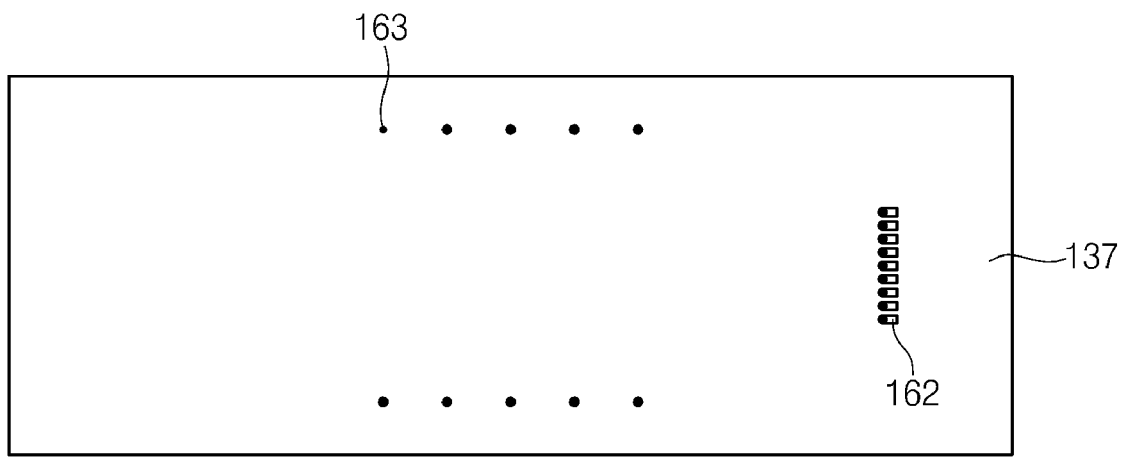

FIG. 6C is a plan view illustrating an upper chip guide of a board circuit part in a bio-sensor chip according to an embodiment of the present invention, and FIG. 6D is a plan view illustrating an upper circuit board of a board circuit part in a bio-sensor chip according to an embodiment of the present invention. FIGS. 6E and 6F are plan views illustrating a lower circuit board of a board circuit part in a bio-sensor chip according to an embodiment of the present invention.

Referring to FIGS. 6B and 6C, the upper chip guide 131a may include the coupling grooves 138 defined in the four edges thereof and a guide groove 135 guiding the sensing part 150 in position. The guide groove 135 may include a first groove 135a for exposing a back substrate bias pad 132 and a second groove 135b for exposing a bonding pad 134.

Referring to FIGS. 6B and 6D, the upper circuit board 131b may include the internal connection pads 132 and 134 electrically connected to the sensing part 150. The internal connection pads 132 and 134 may include the back substrate bias pad 132 and the bonding pad 134. When the sensing part 150 is disposed on the back substrate bias pad 132, a bonding wire 139 may have one end and the other end that are formed of Au and electrically connected to the sensing part 150 and the bonding pad 134, respectively. The internal connection pads 132 and 134 may be formed of a copper foil. A gold foil may be further coated on a surface of the bonding pad 134. A conductive double-sided adhesive carbon tape may be inserted between the semiconductor substrate 151 and the back substrate bias pad 132. For example, one back substrate bias pad 132 may be provided, and four pairs of bonding pads 134 may be provided. The four pairs of bonding pads 134 may correspond to the four groups (reference numeral 152a to 152d of FIG. 5A) of the sensing part 150. For example, a pair of bonding pads 134 may be electrically connected to the sensors 152 included in the one group 152a by the bonding wire 139. The number of pads 132 and 134 is not limited to the above-described number of pads. For example, the larger or smaller number of pads 132 and 134 may be provided.

Referring again to FIG. 6B, the lower circuit board 131c may include a first layer 136 including a plurality of electrical interconnections 161 and a second layer 137 including a plurality of external connection pads 162 electrically connected to the plurality of electrical interconnections 161. The circuit board 131c and 131d may include three layers, i.e., the upper circuit board 131b constituting the highest layer, the first layer 136 constituting a middle layer, and the second layer 137 constituting the lowest layer.

Referring to FIGS. 6B and 6E, for example, the first layer 136 may include total nine electrical interconnections 161 including four pairs of first interconnections 161a electrically connected to the four pairs of bonding pads 134 and one second interconnection 161b electrically connected to the back substrate bias pad 132. The number of electrical interconnections 161 is not limited to the above-described number of interconnections. For example, the larger or smaller number of electrical interconnections 161 may be provided. The electrical interconnections 161 may be formed of a copper foil. Since the first layer 136 is disposed between the upper circuit board 131b and the second layer 137, the plurality of electrical interconnections 161 disposed on the first layer 136 may be protected against external contact or the solution material.

Referring to FIGS. 6B and 6F, for example, the second layer 137 may include nine external connection pads 162 electrically connected to the nine electrical interconnections 161. The number of external connection pads 162 is not limited to the above-described number. For example, the larger or smaller number of external connection pads 162 may be provided. The external connection pads 162 may be electrically connected to the external device such as the reader. Thus, the electrical signal of the sensing part 150 may be transmitted to the reader. The external connection pads 162 may be formed of a copper foil. A gold foil may be coated on surfaces of the external connection pads 162.

A plurality of holes 163 for passing through the first and second layers 136 and 137 may be provided to be socket-coupled to the reader. A metal such as Cu, Au, or Cu/Au may be coated on an inner wall of each of the holes 163.

Another Embodiment

Figure 7A:
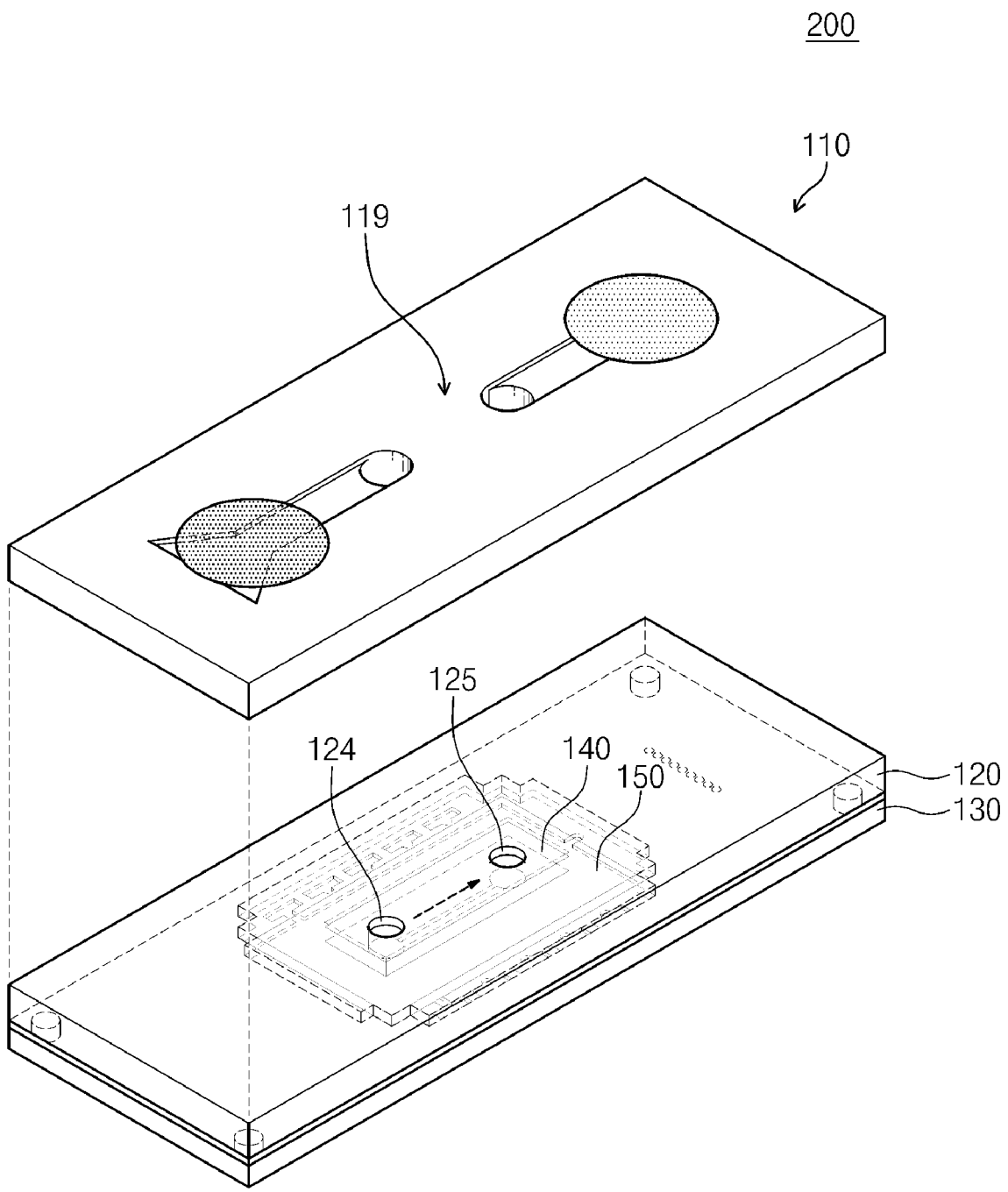
FIG. 7A is a perspective view of a bio-sensor chip according to another embodiment of the present invention.

FIG. 7A is a perspective view of a bio-sensor chip according to another embodiment of the present invention.

Referring to FIG. 7A, a bio-sensor chip 200 according to another embodiment includes an upper cover 110, a lower cover 120, and a board circuit part 130. A solution material containing a target material is introduced and discharged from/into the outside through the upper cover 110. The lower cover 120 covers a sensing part 150 for sensing the introduced solution material and a channel part 140 for moving the solution material to the sensing part 150. The board circuit part 130 transmits an electrical input/output signal between the sensing part 150 and an external device (e.g., reader).

The upper cover 110 and the lower cover 120 may be manufactured as separate structures to form two-layer structure. Alternatively, the upper cover 110 and the lower cover 120 may be integrated in one body to form a single-layer structure.

According to another embodiment, the bio-sensor chip 200 may include a provision part 119 for providing the solution material from the outside and receiving the solution material in which the detection process (sensing process) has been performed to store the solution material. The provision part 119 may be disposed in the upper cover 110.

Figure 7B:
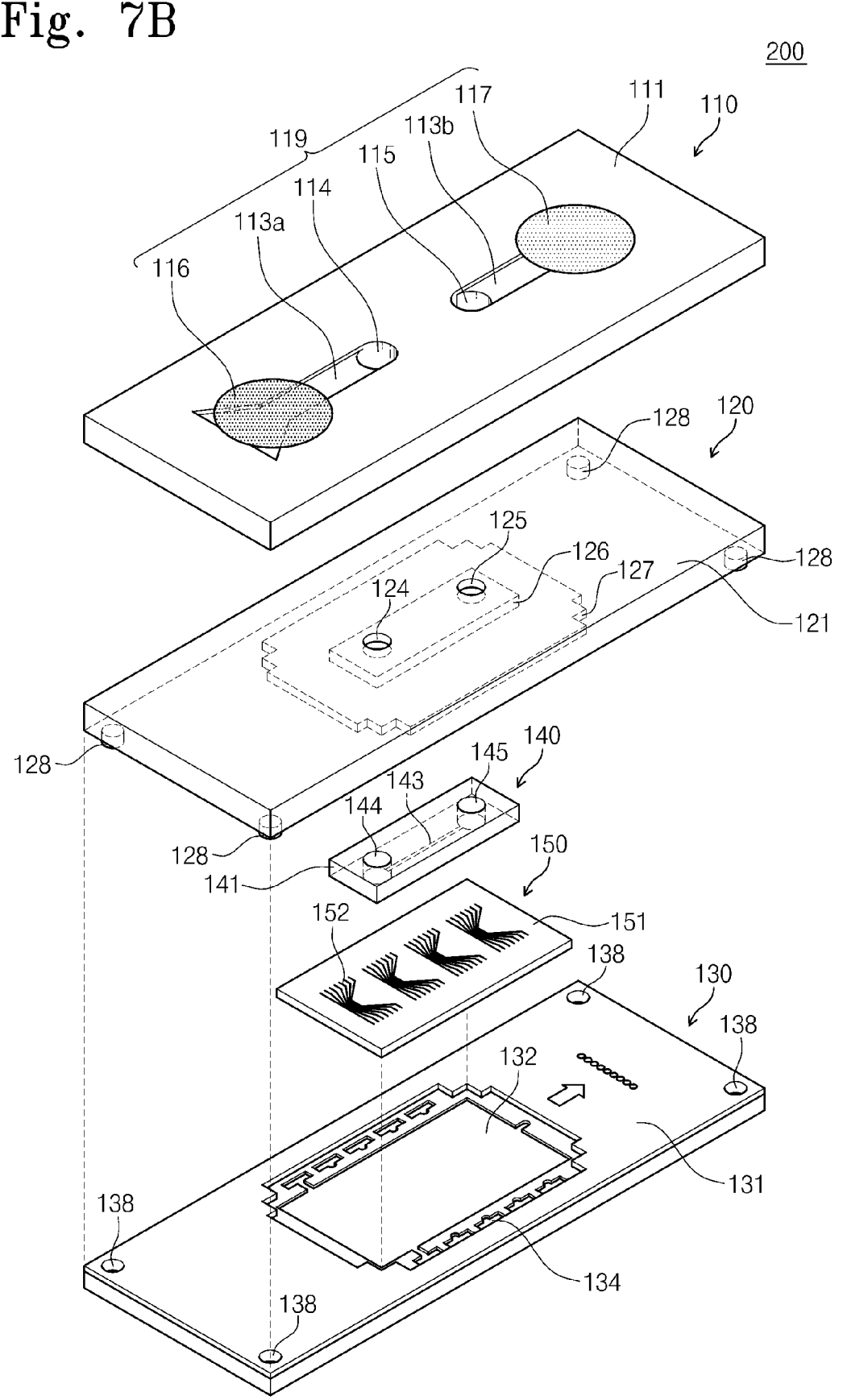
FIG. 7B is an exploded perspective view of a bio-sensor chip according to another embodiment of the present invention.

FIG. 7B is an exploded perspective view of a bio-sensor chip according to another embodiment of the present invention.

Referring to FIG. 7B, as described above, the upper cover 110 may include the provision part 119 for providing the solution material. The provision part 119 may include solution flow channels 113a and 113b for providing moving paths of the solution material, an upper solution inlet 114 for injecting the solution material, and an upper solution outlet 115 for discharging the solution material. A filter 116 for separating a specific component of the solution material may be disposed at one end of the first solution flow channel 113a. A storage container 117 for storing the solution material for which the detection process is already completed may be disposed at one end of the second solution flow channel 113b.

For example, when the solution material is blood, the filter 116 may filter blood corpuscle of whole blood to separate blood plasma or blood serum from the blood. The filter 116 may include a paper filter, e.g., a paper filter commercialized as the model name "MDI-FRI". When the blood is provided into the filter 116, the blood may be absorbed into the filter 116 to remove blood corpuscle components such as red blood cells, white blood cells, and blood platelets. The blood plasma or the blood serum in which the blood corpuscle components of the whole blood are removed may pass through the first solution flow channel 113a. At this time, the blood containing a target material to be detected may reach the upper solution inlet 114 by a capillary action, and then the blood passing through the upper solution inlet 114 may be provided into the sensing part 150 via the channel part 140 to detect the specific component of the blood.

A body 111 of the upper cover 110 may be formed of a transparent material to easily observe a leak state of the solution material from the outside. For example, the body 111 of the upper cover 110 may be formed of one of polymethylmethacrylate, polycarbonate, cyclic olefine copolymer, polyethylene sulfone, polystyrene, and combinations thereof.

The lower cover 120, the channel part 140, the sensing part 150, and the board circuit part 130 may have the substantially same structure as those described with reference to FIGS. 1 through 6F. Roughly explaining, the lower cover 120 and the board circuit part 130 may be inserted into the coupling groove 138, and thus coupled to each other. The channel part 140 and the sensing part 150 may be packaged between the lower cover 120 and the board circuit part 130, which are coupled to each other. The lower cover 120 may include a solution inlet 124 (hereinafter, referred to as a lower solution inlet) vertically aligned with the upper solution inlet 114 and a solution outlet 125 (hereinafter, referred to as a lower solution outlet) vertically aligned with the upper solution outlet 115. The channel part 140 may include a channel solution inlet 144 vertically aligned with the lower solution inlet 124, a channel solution outlet 145 vertically aligned with the lower solution outlet 125, and a fluid channel 143 disposed between the channel inletsolution inlet 144 and the channel solution outlet 145 to guide the solution material such that the solution material crossly flows through sensors 152 of the sensing part 150. The board circuit part 130 may include a printed circuit board 131 on which an electrical circuit coupled to external devices such as a back substrate bias pad 132, a bonding pad 134, and a reader is disposed.

The bio-sensor chip 200 according to another embodiment may easily separate the blood corpuscle and the blood plasma (or the blood serum) from the blood using the filter 116 without employing a centrifugal separator. In addition, the blood may sequentially flow through the upper solution inlet 114, the lower solution inlet 124, and the channel solution inlet 114 to flow into the fluid channel 143. That is, the blood may be moved into the sensing part 150 due to the capillary action without employing a syringe pump. When the blood containing the target material is transferred into the sensing part 150 by the capillary action, the target material interacts with a detection material to cause a change of conductivity. As a result, the existence or concentration of the target material may be detected. The blood for which the detection process is already completed may sequentially discharged through the channel solution outlet 145, the lower solution outlet 125, and the upper solution outlet 115. The discharged blood may flow into the storage container 117 through the second solution flow channel 113b.

The bio-sensor chip according to the embodiment of the present invention has a simple manufacturing process, relatively low manufacturing costs, and easy portability. In addition, the bio-sensor chip can simple detect the target material. Thus, the bio-sensor can be easily used for the medical profession such as a hospital as well as a home. The bio-sensor chip itself can filter the solution material to separate the target material. Thus, the solution material can be easily separated without employing a device such as the centrifugal separator. Also, since the solution material is moved into the sensing part by the capillary action, a device such as the syringe pump may be not required to maximize the portability and usability of the bio-sensor chip.

The embodiment of the present invention can be applied to the semiconductor industry and manufacturing industry for manufacturing bio-sensor chips or medical devices and other health devices.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A bio-sensor chip comprising:
    a sensing part in which a target material and a detection material interact with each other to detect the target material;
    a board circuit part electrically connected to the sensing part;
    a channel part providing a solution material containing the target material into the sensing part; and
    a cover coupled to the board circuit part to cover the channel part and the sensing part,
    wherein the cover includes a first space into which at least a portion of the channel part is inserted, and a second space into which the sensing part is inserted, and
    wherein the cover applies pressure to the channel part to seal a coupling between the channel part and the sensing part so that the solution material flowing along the channel part is prevented from leaking.

2. The bio-sensor chip of claim 1, wherein the cover comprises a solution inlet providing an input path through which the solution material flows into the channel part and a solution outlet providing an output path through which the solution material flows from the channel part.

3. The bio-sensor chip of claim 2, wherein the cover comprises a transparent body formed of one of polymethylmethacrylate, polycarbonate, cyclic olefine copolymer, polyethylene sulfone, polystyrene, and combinations thereof.

4. The bio-sensor chip of claim 2, wherein the channel part comprises:
    a channel inlet vertically aligned with the solution inlet to provide a flow path of the solution material from the solution inlet toward the sensing part;
    a channel outlet vertically aligned with the solution outlet to provide a flow path of the solution material from the sensing part toward the solution outlet; and
    a fluid channel extending from the channel inlet up to the channel outlet to restrict the flow path of the solution material to the sensing part.

5. The bio-sensor chip of claim 4, wherein the channel part comprises a transparent body formed of polydimethylsiloxane.

6. The bio-sensor chip of claim 4, wherein the sensing part comprises:
    a semiconductor substrate; and
    a sensor having a detection material disposed on the semiconductor substrate, wherein the sensor contacts the solution material provided through the channel inlet such that the detection material interacts with the target material.

7. The bio-sensor chip of claim 1, wherein the board circuit part comprises:
    an upper chip guide comprising a guide groove for guiding a position of the sensing part; and
    a lower circuit board electrically connected to the sensing part to input and output an electrical signal of the sensing part.

8. The bio-sensor chip of claim 1, wherein the board circuit part comprises a coupling groove for coupling the cover thereto, and the cover comprises a coupling protrusion inserted into the coupling groove.

9. A bio-sensor chip comprising:
    a sensing part comprising a sensor in which a detection material is fixed and a semiconductor substrate on which the sensor is disposed;
    a channel part providing a solution material containing a target material interacting with the detection material into the sensing part to contact the solution material with the sensor;
    a board circuit part electrically connected to the sensing part to input and output an electrical signal between an external device and the sensing part; and
    a cover covering the board circuit part to provide a space in which the sensing part and the channel part are disposed, the cover providing input and output paths of the solution material, wherein the cover applies pressure to the channel part to seal a coupling between the channel part and the sensing part so that the solution material contacting with the sensor is prevented from leaking.

10. The bio-sensor chip of claim 9, wherein the cover comprises a first transparent cover having a first inlet providing an input path through which the solution material flows into the channel part and a first outlet providing an output path through which the solution material flows from the channel part.

11. The bio-sensor chip of claim 10, wherein the cover further comprises a second transparent cover covering the first transparent cover,
wherein the second transparent cover comprises:
a flow channel providing a flow path of the solution material;
a filter filtering the solution material;
a second inlet providing an input path through which the filtered solution material flows into the first transparent cover and a second outlet providing an output path through which the filtered solution material flows from the first transparent cover; and
a storage container storing the solution material discharged through the second outlet.

12. The bio-sensor chip of claim 9, wherein the sensor comprises:
a plurality of sensor groups independently detecting protein makers different from each other; and
at least one sensor group obtaining a reference signal of an electrical signal change of the sensing part.

13. The bio-sensor chip of claim 9, wherein the board circuit part comprises:
a chip guide comprising a guide groove for guiding a position of the sensing part;
an upper circuit board comprising a substrate bias pad connected to the semiconductor substrate of the sensing part, and a bonding pad connected to the sensing part by a bonding wire; and
a lower circuit board comprising a first layer having a plurality of electrical interconnections connected to the substrate bias pad and the bonding pad, and a second layer having a plurality of connection pads connected to the plurality of electrical interconnections.

14. A bio-sensor chip comprising:
a sensing part comprising a plurality of nano-wire sensors in which a detection material is fixed and a semiconductor substrate on which the plurality of nano-wire sensors are disposed;
a transparent channel part guiding a solution material containing a target material interacting with the detection material such that the solution material flows through the plurality of nano-wire sensors;
a board circuit part electrically connected to the sensing part to input and output an electrical signal between an external device and the sensing part;
a lower transparent cover covering the board circuit part to provide a space in which the sensing part and the channel part are disposed; and
an upper transparent cover covering the lower transparent cover,
wherein the lower transparent cover applies pressure to the channel part to seal a coupling between the channel part and the sensing part so that the solution material flowing through the plurality of nano-wire sensors is prevented from leaking.

15. The bio-sensor chip of claim 14, wherein the lower transparent cover comprises a lower solution inlet providing an input path through which the solution material flows into the transparent channel part and a lower solution outlet providing an output path through which the solution material flows from the transparent channel part.

16. The bio-sensor chip of claim 15, wherein the upper transparent cover comprises:
an upper solution inlet and an upper solution outlet, which are vertically aligned with the lower solution inlet and the lower solution outlet, respectively;
a filter filtering the solution material provided into the upper solution inlet;
a storage container storing the solution material discharged from the upper solution outlet;
a first solution flow channel providing a flow path of the solution material from the filter toward the upper solution inlet; and
a second solution flow channel providing a flow path of the solution material from the upper solution outlet toward the storage container.

17. The bio-sensor chip of claim 16, wherein the transparent channel part comprises:
a channel solution inlet and a channel solution outlet, which are vertically aligned with the lower solution inlet and the lower solution outlet, respectively; and
a fluid channel extending from the channel solution inlet up to the channel solution outlet to allow the solution material to flow on the plurality of nano-wire sensors.

18. The bio-sensor chip of claim 14, wherein the nano-wire sensor comprises:
a silicon nano-channel doped with impurities contacting with the solution material; and
a source/drain disposed at both sides of the silicon nano-channel.

19. The bio-sensor chip of claim 14, wherein the board circuit part comprises:
an upper chip guide comprising a guide groove for guiding a position of the sensing part and a coupling groove for coupling the lower transparent cover thereto; and
a lower printed circuit board comprising an internal connection pad connected to the sensing part, an electrical interconnection electrically connected to the internal connection pad, and an external connection pad connected to the electrical interconnection.

20. The bio-sensor chip of claim 19, wherein the lower transparent cover comprises a coupling protrusion inserted into the coupling groove.

* * * * *